(12) United States Patent
Park (10) Patent No.: US 7,829,325 B2
(45) Date of Patent: Nov. 9, 2010

(54) DRUG TESTING WITH BIO-ARTIFICIAL ORGAN SLICES INCLUDING FOR EXAMPLE THOSE DERIVED FROM LIVER

(75) Inventor: Sung-Soo Park, Rancho Palos Verdes, CA (US)

(73) Assignee: HepaHope, Inc., Irvine, CA (US)

( * ) Notice: Subject to any disclaimer, the term of this patent is extended or adjusted under 35 U.S.C. 154(b) by 559 days.

(21) Appl. No.: 11/210,511

(22) Filed: Aug. 24, 2005

(65) Prior Publication Data

US 2005/0282152 A1    Dec. 22, 2005

Related U.S. Application Data

(62) Division of application No. 10/738,905, filed on Dec. 16, 2003, now abandoned.

(51) Int. Cl.
*A01N 1/02* (2006.01)
(52) U.S. Cl. .................. 435/284.1; 435/286.5; 435/1.1; 435/286.6; 435/299.1; 435/335; 435/395; 435/174; 435/176; 422/102
(58) Field of Classification Search .............. 435/386.5, 435/1.2, 4, 325, 370, 284.1, 286.6, 299.1, 435/394, 395, 396, 1.1, 286.5, 174, 176, 435/335; 422/102
See application file for complete search history.

(56) References Cited

U.S. PATENT DOCUMENTS

| 4,308,351 | A | 12/1981 | Leighton et al. |
| 4,559,299 | A | 12/1985 | Rotman |
| 5,773,285 | A | 6/1998 | Park |
| 5,866,420 | A | 2/1999 | Talbot et al. |
| 5,932,459 | A | 8/1999 | Sittinger |
| 5,976,870 | A | 11/1999 | Park |
| 6,218,182 | B1 | 4/2001 | Naughton |
| 6,852,505 | B1 | 2/2005 | Yeh |

(Continued)

FOREIGN PATENT DOCUMENTS

JP    08-163996 A    6/1996

(Continued)

OTHER PUBLICATIONS

Download from "Merriam Webster Online Dictionary" for definition of "ostensive" from http://m-w.com/dictionary/ostensrive; obtained Dec. 13, 2007, 1 page.*

(Continued)

*Primary Examiner*—Sandra Saucier
*Assistant Examiner*—Susan Hanley
(74) *Attorney, Agent, or Firm*—Greenberg Traurig LLP (57) ABSTRACT

A drug testing system using any number of bio-artificial organs, for example liver-slices based in a culture apparatus. The apparatus has a chamber with plasma and gas valves, animal organ slices being positioned securely in the chamber so as to maximize the surface area of organ slices exposed to the culture medium. Plasma is supplied to the chamber so that it rises to contact the organ slices, and is alternately removed from contacting the organ slices. Gas is supplied to the top of the chamber. The system also includes a reservoir for containing media entering and exiting the chamber. Methods are provided for assessing the toxicity of a drug or drug candidate.

11 Claims, 6 Drawing Sheets

U.S. PATENT DOCUMENTS

| | | |
|---|---|---|
| 2004/0185558 A1 | 9/2004 | Griguer |
| 2004/0265997 A1 | 12/2004 | Park |
| 2005/0130254 A1 | 6/2005 | Park |

FOREIGN PATENT DOCUMENTS

| | | |
|---|---|---|
| JP | 2002 233361 A | 8/2002 |
| WO | WO 97/12960 A | 4/1997 |
| WO | WO 2005/061694 A1 | 7/2005 |

OTHER PUBLICATIONS

Sato A: "Cancer Chemotherapy with Oriental Medicine (I): Antitumoractivity of Crude Drugs with Human Tissue Cultures in in Vitro Screening". International Journal of Oriental Medicine, Ohai Press, Long Beach, CA, US, vol. 15, No. 4, Dec. 1, 1990, pp. 171-183, XP001098648 ISSN: 1044-0003.

Farkas Dora, et al.: "In vitro methods to study chemically-induced hepatotoxicity: A literature review" Current Drug Metabolism, vol. 6, No. 2, Apr. 2005, pp. 111-125, XP008094939; ISSN: 1389-2002; whole document; p. 112-p. 113.

Jan. 7, 2009 letter forwarding EP Supplemental Search Report for EP application No. 06802350.6; received by Applicant(s) Attorney of Record on Jan. 7, 2009.

EP Supplemental Search Report—EP application No. 06802350.6.

Feb. 24, 2009 letter forwarding EP Supplemental Search Report for EP application No. 06802349.8; received by Applicant(s) Attorney of Record on Mar. 3, 2009.

EP Supplemental Search Report—EP application No. 06802349.8.

Mar. 17, 2009 letter forwarding SG Written Opinion for SG application No. 200801535-6; received by Applicant(s) Attorney of Record on Mar. 18, 2009.

SG Written Opinion—SG application No. 200801535-6.

Vickers et al; "Organ Slice Viability Extended for Pathway Characterization; An In Vitro Model to Investigate Fibrosis" Toxicological Sciences 2004, vol. 82, No. 2; pp. 534-544.

Frankmoelle et al; "Glutathione S-Transferase Metabolism of the Antineoplastic Pentafluorophenylsulfonamide in Tissue Culture and Mice" Drug Metabolism and Disposition, vol. No. 8, pp. 951-958, 2000.

Fisher et al; "Cold-and Cryopreservation of Dog Liver and Kidney Slices" Cryobiology 1996, vol. 33, pp. 163-171.

\* cited by examiner

DRUG TESTING WITH BIO-ARTIFICIAL ORGAN SLICES INCLUDING FOR EXAMPLE THOSE DERIVED FROM LIVER

RELATED APPLICATION

This application is a division of U.S. Utility patent application Ser. No. 10/738,905, entitled "Drug Testing System With Bio-Artificial Liver," filed on Dec. 16, 2003, now abandoned. The contents of that application are incorporated expressly by reference herein, as if fully set forth and full Paris Convention Priority is hereby expressly claimed.

Likewise, expressly incorporated by reference herein are U.S. Pat. No. 5,773,285 issued Jun. 30, 1998, U.S. Pat. No. 5,795,710 issued Aug. 18, 1998 and U.S. Pat. No. 5,976,870 issued Nov. 2, 1999. Also incorporated by reference herein are PCT Application Nos. US/04/015824 and US/04/16477.

BACKGROUND

The invention relates to a drug testing system with biological artificial organ slices, including those derived from liver and, more particularly, a bioreactor for evaluation, detection and testing of drug candidates, drugs and drug metabolites.

In 2001, the average cost to develop a new drug exceeded $800 million, according to a study by the Tufts Center for the Study of Drug Development. Of this, approximately $16 million on average per company was used for pre-clinical research. Reduction of testing time and cost in drug development is therefore a critical factor to the survival of most pharmaceutical companies. In addition, since there is usually more than one company competing in the same drug arena, any competitive advantage would be welcome. A major portion of drug development costs is borne during the FDA approval process. However, much of this cost cannot be managed in the same way that pre-clinical costs can. To address soaring pre-clinical costs, more efficient, affordable, and timely methods of in vivo and in vitro testing and selection of potential new drug candidates are of significant interest in the industry.

In developing a new drug, toxicity is always an important consideration. Since the liver metabolizes most drugs, liver damage is of great concern. Likewise, other organs and systems, and how they react to foreign substances, is extremely important. Conventional in vivo and in vitro tests utilizing small animals and cell culture techniques are therefore widely used to assess liver function in drug development. However, these conventional tests have particular disadvantages, such as individual variation, high costs to use large animals, and loss of naturally existing characteristics of liver in situ. The same is true for other organs.

To overcome these disadvantages, cell culture systems have also been used. However, with these models cell-to-cell connective interactions cannot be maintained for a desired length of time. This leads to failure of the testing scheme, which is not directed to organ or organ system response.

Bioartificial organ devices are currently being developed. It is believed that organ function can only be replaced with the biological substrate, that is, for example, liver cells or a whole liver specimen, which requires the availability of liver tissue from xenogenic or human sources. Recent efforts have combined mechanical and biologic support systems in hybrid liver support devices. The mechanical component of these hybrid devices serves both to remove toxins and to create a barrier between the patient's serum and the biologic component of the liver support device. The biologic component of these hybrid liver support devices may consist of liver slices, granulated liver, or hepatocytes from low-grade tumor cells or porcine hepatocytes. These biologic components are housed within chambers often referred to as bioreactors. However problems remain with respect to maintaining the functionality of the individual cell lines used in these devices. Most devices use immortalized cell lines. It has been found that over time these cells lose specific functions.

There are several groups developing bioartificial liver devices, for example, Circe Biomedical® (Lexington, Mass.), Vitagen® (La Jolla, Calif.), Excorp Medical (Oakdale, Minn.), and Algenix (Shoreview, Minn.). The Circe Biomedical device integrates viable liver cells with biocompatible membranes into an extracorporeal, bioartificial liver assist system. Vitagen's ELAD® (Extracorporeal Liver Assist Device) Artificial Liver is a two-chambered hollow-fiber cartridge containing a cultured human liver cell line (C3A). The cartridge contains a semipermeable membrane with a characterized molecular weight cutoff. This membrane allows for physical compartmentalization of the cultured human cell line and the patient's ultrafiltrate. Algenix provides a system in which an external liver support system uses porcine liver cells. Individual porcine hepatocytes pass through a membrane to process the human blood cells. Excorp Medical's device contains a hollow fiber membrane (with 100 kDa cutoff) bioreactor that separates the patient's blood from approximately 100 grams of primary porcine hepatocytes that have been harvested from, purpose-raised, pathogen-free pigs. Blood passes though a cylinder filled with hollow polymer fibers and a suspension containing billions of pig liver cells. The fibers act as a barrier to prevent proteins and cell byproducts of the pig cells from directly contacting the patient's blood but allow the necessary contact between the cells so that the toxins in the blood can be removed.

Various aspects of these devices represent improvements over pre-existing technology, but they still have particular disadvantages. The effectiveness of these devices, all of which use individual hepatocytes, is limited due to the lack of cell-to-cell interactions, which characterize the liver in its in vivo state. Accordingly, a bioartificial organ, for example a liver with improved efficiency, viability, and functionality for use in drug development would be beneficial. This longstanding need is addressed by the instant teachings, which provide for drug testing with bio-artificial organ slices.

SUMMARY

It is one object of the present invention to provide a system to test the toxicity of a potential drug candidate and its metabolites, on various organs.

The present invention provides a system for testing a potential drug candidate for toxicity. The system has an organ slice culture apparatus made up of a chamber having a medium inlet and a gas valve, a plurality of animal organ slices positioned securely within the chamber so as to maximize the surface area of the organ slices exposed to the medium, means for selectively supplying and removing a medium in the chamber so that the medium in the chamber comes into contact with the organ slices, and is removed from contact with the organ slices, and a reservoir for containing the medium as it enters and exits the chamber. The organ slices are cultured in an environment of an oxygenated gas under the supply of the medium at regular intervals so that said slices are exposed alternately to the medium and to the gas. When the organ slices are exposed to the potential drug candidate the toxicity of the potential drug candidate can be determined by observing the effectiveness of the organ slices to metabolize a compound in the presence of the potential drug candidate.

In a further embodiment, the system has a mesh at least partially surrounding the organ slices so as to form a space and to retain the slices within this space. In this embodiment the mesh is approximately vertical in the chamber. Additional embodiments have two meshes at least partially surrounding the organ slices.

The invention also provides methods for evaluating the toxicity of a drug. The methods involve supplying a culture medium, contacting the culture medium with organ slices, where the organ slices are positioned securely in a chamber so as to maximize the surface area of liver slices exposed to the culture medium. The chamber has a plasma inlet and a gas valve, means for selectively supplying and removing plasma in the chamber so that the plasma in the chamber comes into contact with the liver slices, and is removed from contact with the organ slices, means for supplying a gas to the chamber, and a reservoir for containing plasma as it enters and exits the chamber. The method further involves contacting the organ slices with a gas mixture of oxygen and carbon dioxide, exposing the organ slices alternately to plasma and the gas mixture of oxygen and carbon dioxide gas, and exposing the organ slices to the drug to be tested. When the organ slices are exposed to the drug the toxicity of the drug can be determined by observing the effectiveness of the organ slices to metabolize a compound in the presence of the drug.

In the embodiments disclosed herein, the compound to be metabolized can be selected from the group consisting of ammonia and lidocaine, and related compounds.

DRAWINGS

Further particularities and advantages of the invention will become clear from the following description of preferred embodiment, with reference to the drawing, in which.

DETAILED DESCRIPTION

The objective during the pre-clinical drug development stage is for a pharmaceutical company to show that the compound is reasonably safe for use in the next phase, which is small-scale clinical studies. The compound's toxic and pharmacologic effects are realized through in vivo and in vitro animal testing. At a minimum, the FDA will ask the pharmaceutical company to: (1) develop a pharmacologic profile of the drug; (2) determine the acute toxicity of the drug in at least two species of animals; and (3) conduct short-term toxicity studies ranging from 2 weeks to 3 months, depending on the proposed duration and use of the substance in the proposed clinical studies. The process is complicated and costly with hundreds and sometimes thousands of compounds being tested.

This testing is often performed by an independent third party in order to rule out any appearance of bias. Every effort is made to ensure that as few animals as possible are used, and that they are treated humanely. Usually two species of animals, one rodent and one non-rodent are used because a drug may affect one species differently than another. Since most drugs are metabolized in the liver, toxicity studies naturally focus on the effects on the liver. Other organs likewise provide key data and are useful within the scope of the present invention.

The present invention, by using organ slices, is ideally suited to the pre-clinical development process. The number of animals required is minimized, as is the need for subjecting the animal to often stressful and painful testing procedures.

In accordance with the present invention, there is provided a bioartificial organ system for evaluation, detection and testing of drug candidates, drugs and drug metabolites. The system has an organ slice culture apparatus.

In one embodiment of the present invention, the apparatus has a chamber with a gas valve, and a plurality of animal liver slices positioned securely within the chamber so as to maximize the surface area of the liver slices exposed to a medium. There is a means for selectively supplying and removing culture medium to the chamber so that the culture medium in the chamber rises to come into contact with the organ slices. The culture medium rises in the chamber so that the liver slices are completely immersed. This means is also able to remove the culture medium from contact with the organ slices. In additional embodiments, there is also a means for supplying a gas to the top of the chamber so that the organ slices are exposed alternately to the gas and to the culture medium. Additionally, a reservoir is provided for containing the culture medium as it enters and exits the chamber. The chamber is preferably thermoregulated. For human organ slices, the temperature is preferably kept at about 36.5 degrees C. For rodent organ slices, it is kept between about 36 to 38 degrees C. However, pig organ slices are very sensitive to temperature fluctuation and it must be maintained at 38 degrees C., the normal body temperature of pigs.

Figure 1:
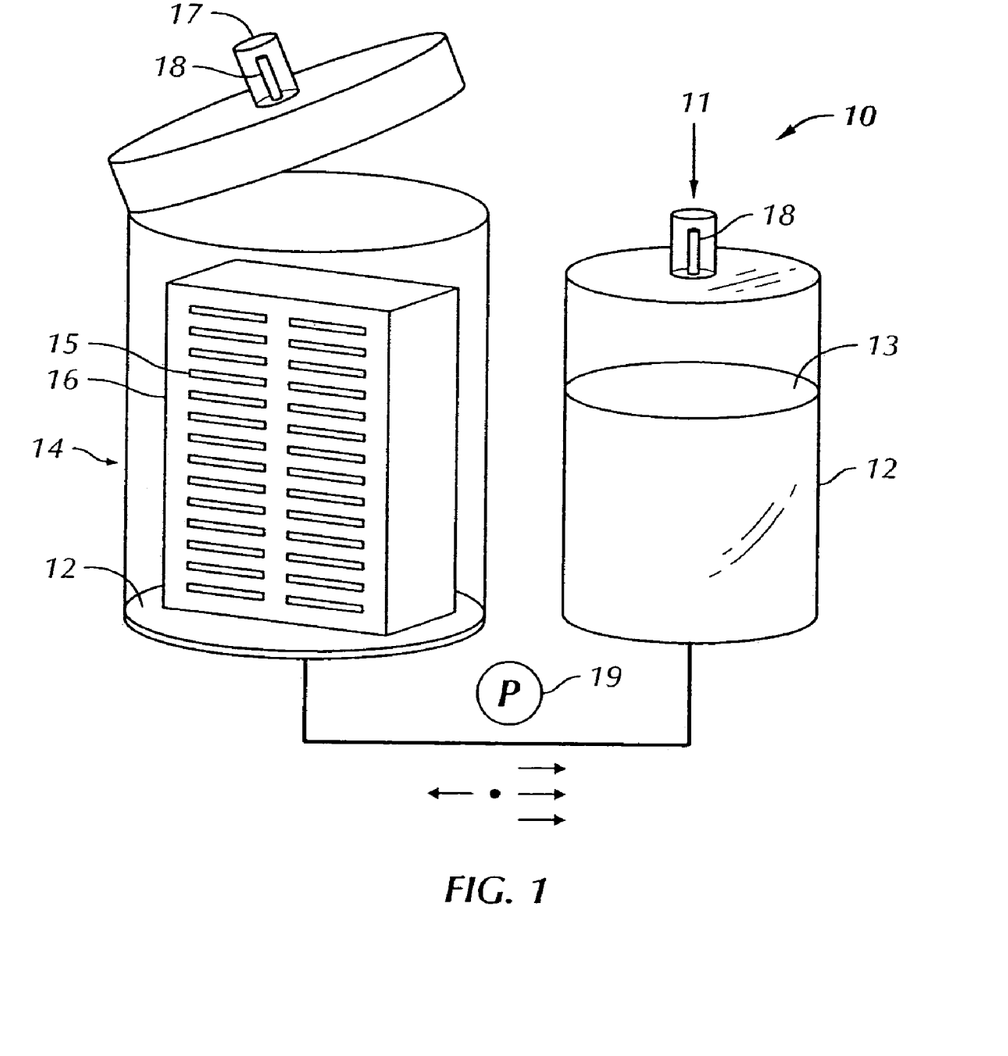
FIG. 1 is a schematic diagram of a system of the present invention.

FIG. 1 is a schematic representation of drug testing system 10 in accordance with the present invention. From reservoir 12 culture medium 13 is introduced into the organ slice culture apparatus 14. Organ slices 15 are arranged between two wire meshes 16 and placed vertically parallel within the bioreactor. As culture medium is introduced into the bioreactor, the fluid level begins to rise until it comes into contact with the organ slices, and eventually the organ slices are completely immersed.

Oxygenated gas is introduced by gas valve 17 in the top of the chamber. Although the gas valve is shown in the top of the chamber, it is also contemplated herein that the gas valve could be on the side or bottom of the chamber, provided with an appropriate seal to prevent leakage of liquid medium. The gas is preferably a mixture of 95% by volume $O^2$ and 5% by volume $CO^2$, and is supplied at a pressure ranging from 1 to 10 ATM to the chamber through the gas valve and discharged therefrom, while controlling the pressure by a pressure controller (not shown). A solenoid valve (also not shown) may be coupled with the pressure controller to maintain a pre-set gas pressure. Gas sterilizing device 18, for example, a syringe filter having a pore size of about 0.22 µm, is preferably installed in gas valve 17 to filter out microbes, thereby sterilizing the supply gas to the chamber. Gas check valve 11 with gas sterilizing device 18 is positioned on the medium reservoir and serves to equalize the pressure between the reservoir and atmosphere.

Stabilization of the organ slices is an important feature of the invention. The organ slices are cultured under the supplies of liquid culture medium and an oxygenated gas. The liquid culture medium, or the plasma, is supplied through the reservoir into the chamber and the oxygenated gas is supplied through the top of the chamber. Each is supplied at regular intervals so that each of the organ slices is exposed alternately to the medium and to the gas at an exposure-time ratio ranging from about 1:2 to about 1:4, preferably about 1:2.5 to about 1:3.5, and most preferably about 1:3. Pump 19 controls the flow of the culture medium.

Although plasma is a relatively good medium to maintain cell viability, there are too many unknown factors present and therefore the results vary from animal to animal. In the present invention Waymouth MB 752/1 medium is preferred over plasma. To prevent central necrosis, the gas mixture described above, 95% $O^2$ and 5% $CO^2$, is preferably used. Since this mixture may produce free oxygen radicals, which are very toxic to liver cells, a high concentration of glutathione and vitamin E, as oxygen free radical scavengers and anti-oxidants, are added. For use of this medium, the formula should be supplemented with 10% complement inactivated Fetal Vovine of Calf Serum and L-Glutamine.

Figure 2A:
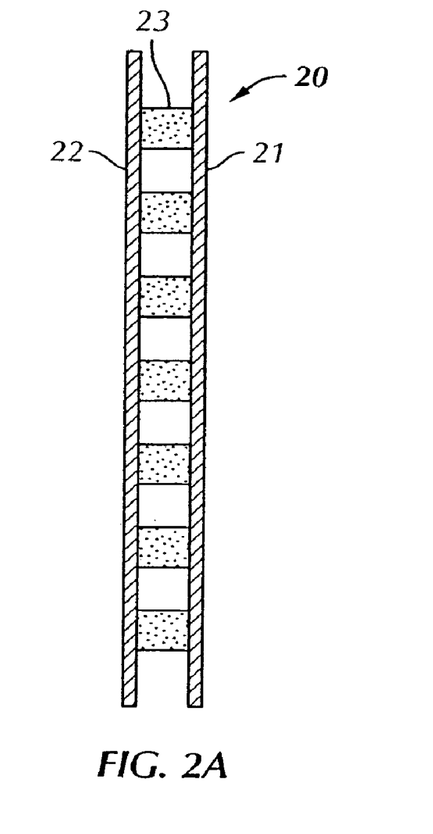
FIG. 2A is a side sectional view of an organ slice arrangement of the present invention.
Figure 2B:
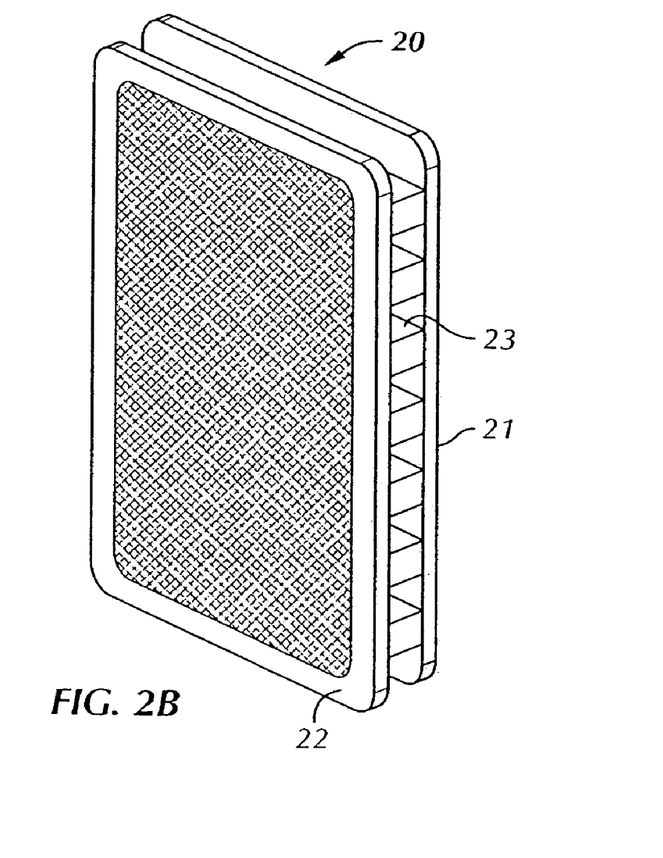
FIG. 2B is a perspective view of the organ slice arrangement of FIG. 2A.

Referring now to the drawing, and more particularly FIGS. 2A and 2B, the organ slice apparatus of the present invention is shown, as represented by numeral 20. Two stainless steel meshes 21 and 22 are provided, the size of which can be chosen based on the dimensions of the chamber. These two meshes are preferably arranged in parallel. In a preferred embodiment, the meshes have about a 0.26 mm pore size. Also, in a preferred embodiment, the meshes are pressed to ensure consistent flatness. Between meshes 21 and 22 is a plurality of liver-slices 23 arranged in an orderly fashion. The two meshes are positioned on each side of the organ slices with enough room so as to not crush the organ slices, but also so as to hold them sufficiently so that they do not get washed away by the plasma. Although FIGS. 2A and 2B show a relatively small number of organ slices positioned between the meshes, it is to be understood that the efficiency of the apparatus is dependent upon the number of organ slices employed. In addition, although two meshes are shown, it is contemplated herein that a single mesh may be used. That mesh is formed to surround, at least partially, the organ slices thereby forming a space and to retain them in that space. For example, the mesh could be formed in a suitably dimensioned U-shape.

Liver slices used in the present invention may be obtained from a suitable animal, for example, a rabbit, pig, dog, rodent, or human, depending on the intended use of the apparatus. Also, they may be of any size or shape suitable for maintaining the viability and essential functions thereof. In the present invention the organ slices are preferred to have a thickness ranging from about 10 μm to about 2,000 μm, and more preferably ranging from about 100 μm to about 500 μm.

The present invention is ideally suited to testing the toxicity and efficiency of a drug. This testing is accomplished by exposing the organ slices to a drug or drug candidate and observing the ability of the liver slices to metabolize a compound, which compound or its metabolites can be detected. For example, ammonia and lidocaine are common compounds that can be metabolized by healthy organ tissue. The following example shows this testing, as applied to liver-slices, as those skilled in the art will recognize also applies to other organs.

EXAMPLE 1

In Vitro Performance

The following example illustrates the in vitro performance of the system using liver slices and forms the model for the drug testing system of the present invention. The example here shows the efficiency of liver slices to metabolize ammonia and lidocaine in the presence of drug candidate HL100.

The liver converts ammonia to urea, which is excreted into the urine by the kidneys. In the presence of severe liver disease, ammonia accumulates in the blood because of both decreased blood clearance and decreased ability to form urea. Elevated ammonia levels can be toxic, especially to the brain, and play a role in the development of hepatic encephalopathy. Accordingly, measuring ammonia clearance can assess liver function. More specifically, measuring ammonia clearance provides an indication of the operability of the present invention to metabolize compounds that may or may not be harmful to the liver.

In addition, lidocaine is a drug that can be converted by the liver from a toxic form into a non-toxic metabolite known as dimethyl xylidine (DMX). The measure of lidocaine clearance is an indication of the performance of the present invention. By measuring the clearance of ammonia or lidocaine in the presence of the drug candidate, a toxicity profile for the drug candidate can be generated. If the drug candidate is toxic to liver cells, there will be a build-up of ammonia and lidocaine in these examples. Therefore there is an observable direct relationship between drug candidate toxicity and lidocaine or ammonia levels.

A 3 to 3.5 kg rabbit was euthanized and liver slices obtained. The slices were approximately 1 cm in diameter with an average weight of 50 mg. Approximately 2 grams total were used in this example. The slices were then pre-cultured by immersion in approximately 200 ml of Williams E media with 10% FCS and drained upon exposure to an oxygenated gas. Each liver slice is exposed alternately to the medium and to the gas at an exposure-time ratio of approximately 1:3.

The gas mixture, approximately 95% oxygen, 5% $CO^2$ at 1 ATM, was maintained in the chamber throughout the study. The gas mixture was exchanged every twelve minutes. Bolus doses of lidocaine (2 mg) or ammonia (20 mg) were injected. The ammonia and DMX were measured by collecting samples at 0, 5, 15, 30, 60, 90 and 120 minutes, after 6 hours and 25 hours of cultivation. The results are summarized in FIGS. 3A, 3B, 4 and 5.

Figure 3A:
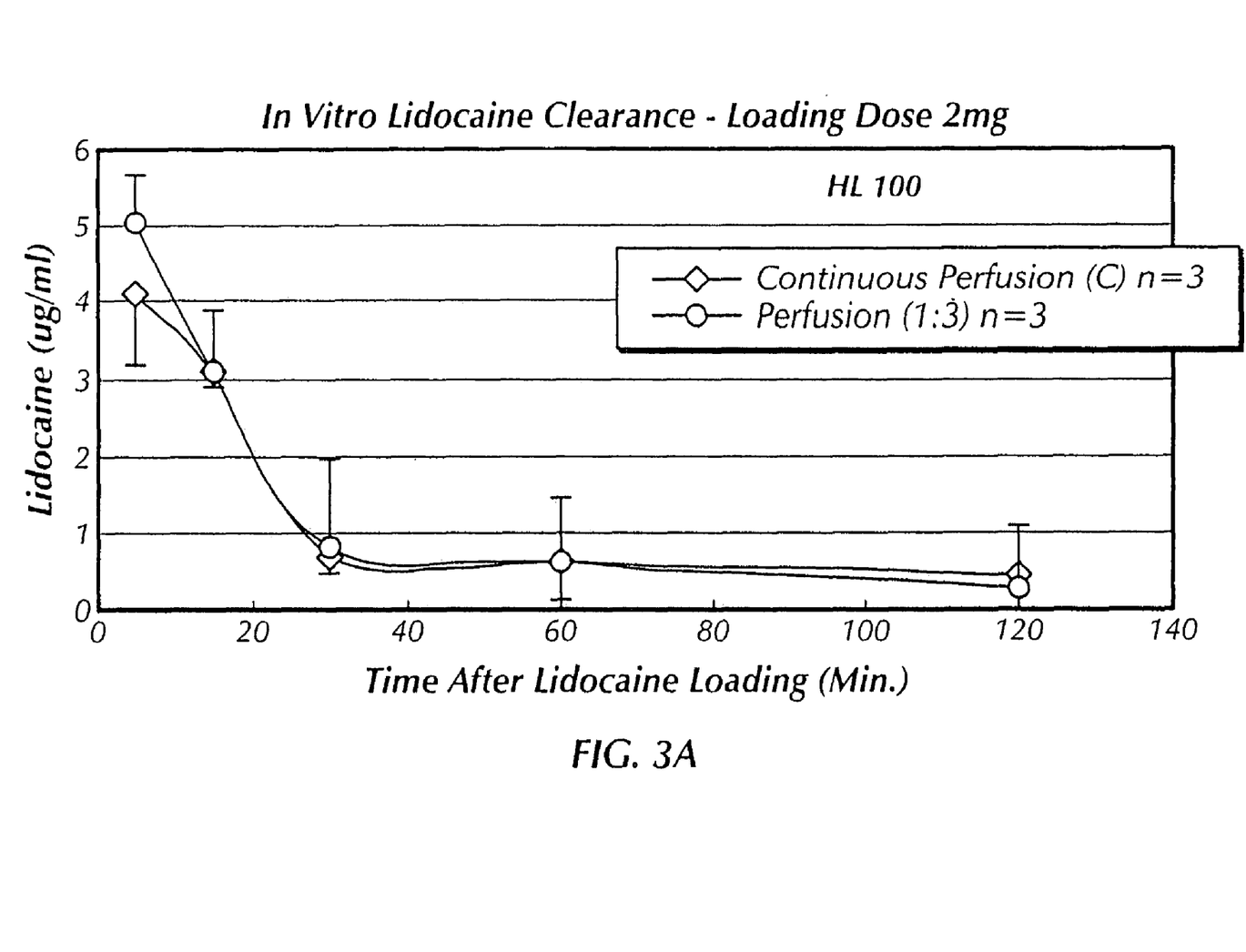
FIG. 3A is a graphical representation of in vitro lidocaine clearance with continuous and intermittent perfusion using a bioartificial organ system of the present invention.

FIG. 3A is a graphical representation of in vitro clearance of a 2 mg dose of lidocaine. Continuous perfusion was performed (as indicated by the diamonds) and intermittent perfusion (time-exposure ratio of 1:3) was also performed (indicated by the circles). Three separate trials were performed for each. At approximately 30 minutes after lidocaine loading, the level of lidocaine dropped from between 3.2 and 5.8 μg to approximately 0.9 μg. This level was reduced to approximately 0.5:g at 120 minutes. The results demonstrate that the device of the present invention reduced lidocaine levels to non-toxic levels within 30 minutes even in the presence of drug candidate HL 100. As compared to continuous medium perfusion, the intermittent perfusion (approximately 1:3) requires less volume of medium while achieving substantially the same results. The results show that the drug candidate does not substantially impair the ability of the liver slices to metabolize lidocaine.

Figure 3B:
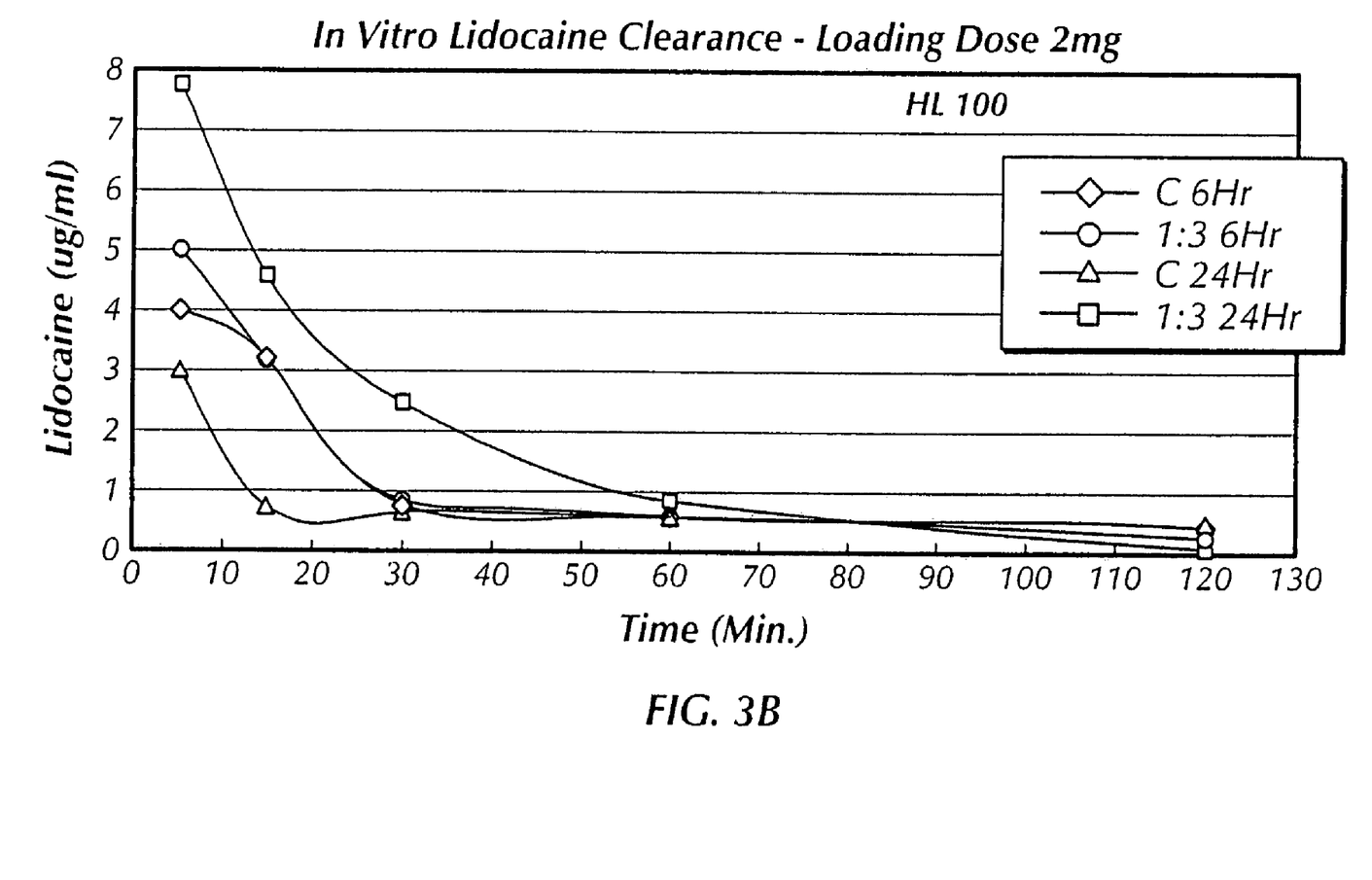
FIG. 3B is a graphical representation of in vitro lidocaine clearance with a 6 hour and a 24 hour run using the bioartificial organ system of the present invention.

FIG. 3B is a graphical representation of in vitro clearance of a 2 mg dose of lidocaine for prior run times of 6 hours and 24 hours. In these runs, the liver slices were exposed to gas either continuously or intermittently in a ratio of 1:3 for 6 hours and for 24 hours prior to lidocaine loading. Initial readings of lidocaine were between 2 μg and 7.8 μg. However, within 30 minutes lidocaine levels reduced to approximately 0.8 μg for the 6 hour trials and for the continuous perfusion 24 hour trial. Within 60 minutes all trials were showing lidocaine levels between 7.7 μg to 1 μg. Again, the results demonstrate the efficiency of the device to reduce lidocaine levels to non-toxic levels with intermittent perfusion while exposed to HL 100.

Figure 4:
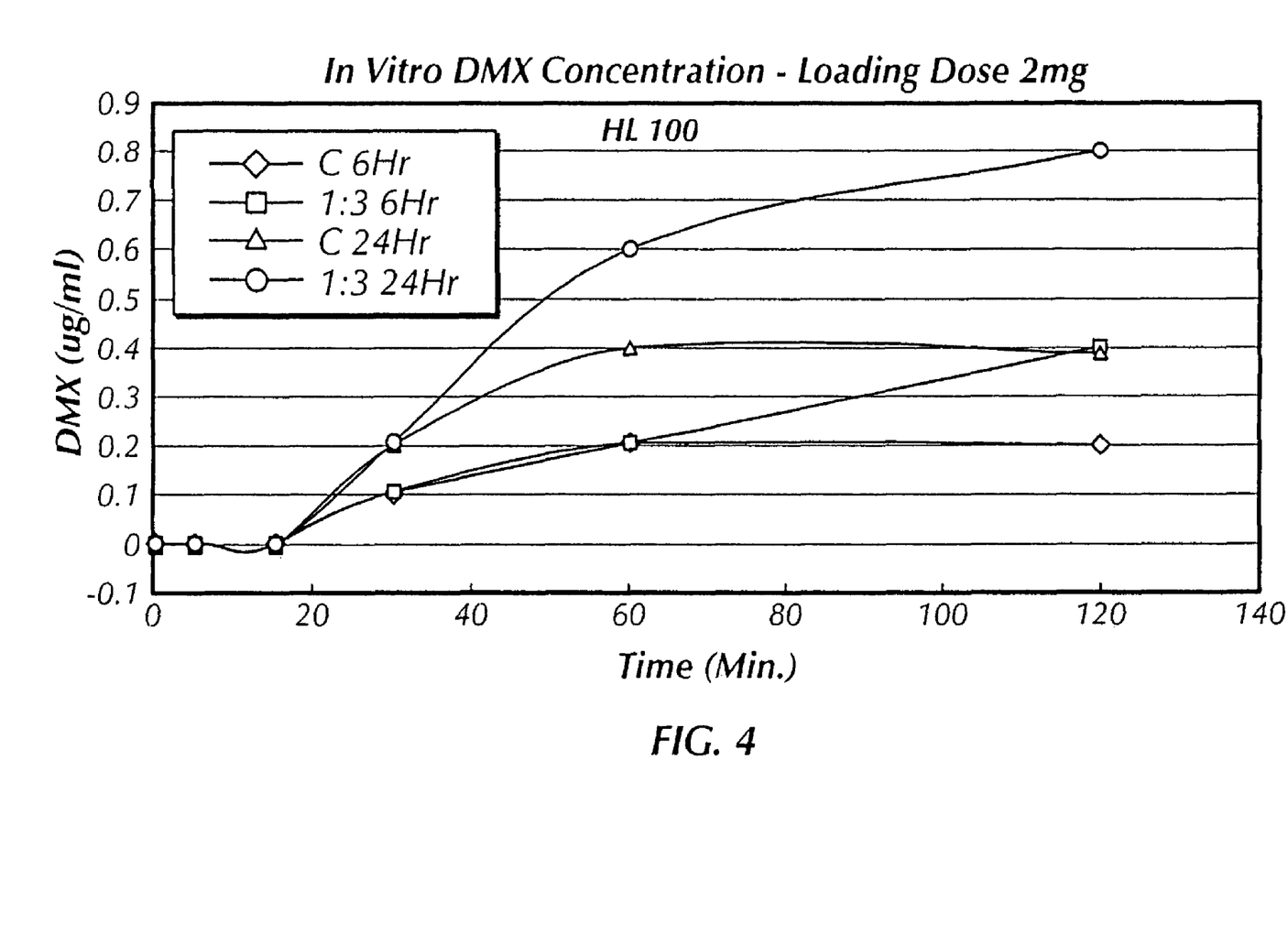
FIG. 4 is a graphical representation of in vitro DMX concentration with a 6 hour and a 24 hour run using the bioartificial organ system of the present invention.

FIG. 4 is a graphical representation of in vitro DMX concentration build-up from a 2 mg lidocaine dose. Initially DMX Concentration remained approximately zero, until approximately 18 minutes. The DMX metabolites were observed increasing in concentration after 18 minutes and reached approximately maximal values at 60 minutes. However, for the 24 hour 1:3 exposure trial, the DMX concentration continued to increase up to 120 minutes. These results show the ability of the present invention to metabolize lidocaine (as indicated by the DMX metabolite concentration increasing over time) in the presence of HL 100. There was no significant difference between the continuous perfusion trial and the intermittent perfusion trial, except for the 24 hour exposure trial mentioned above.

Figure 5:
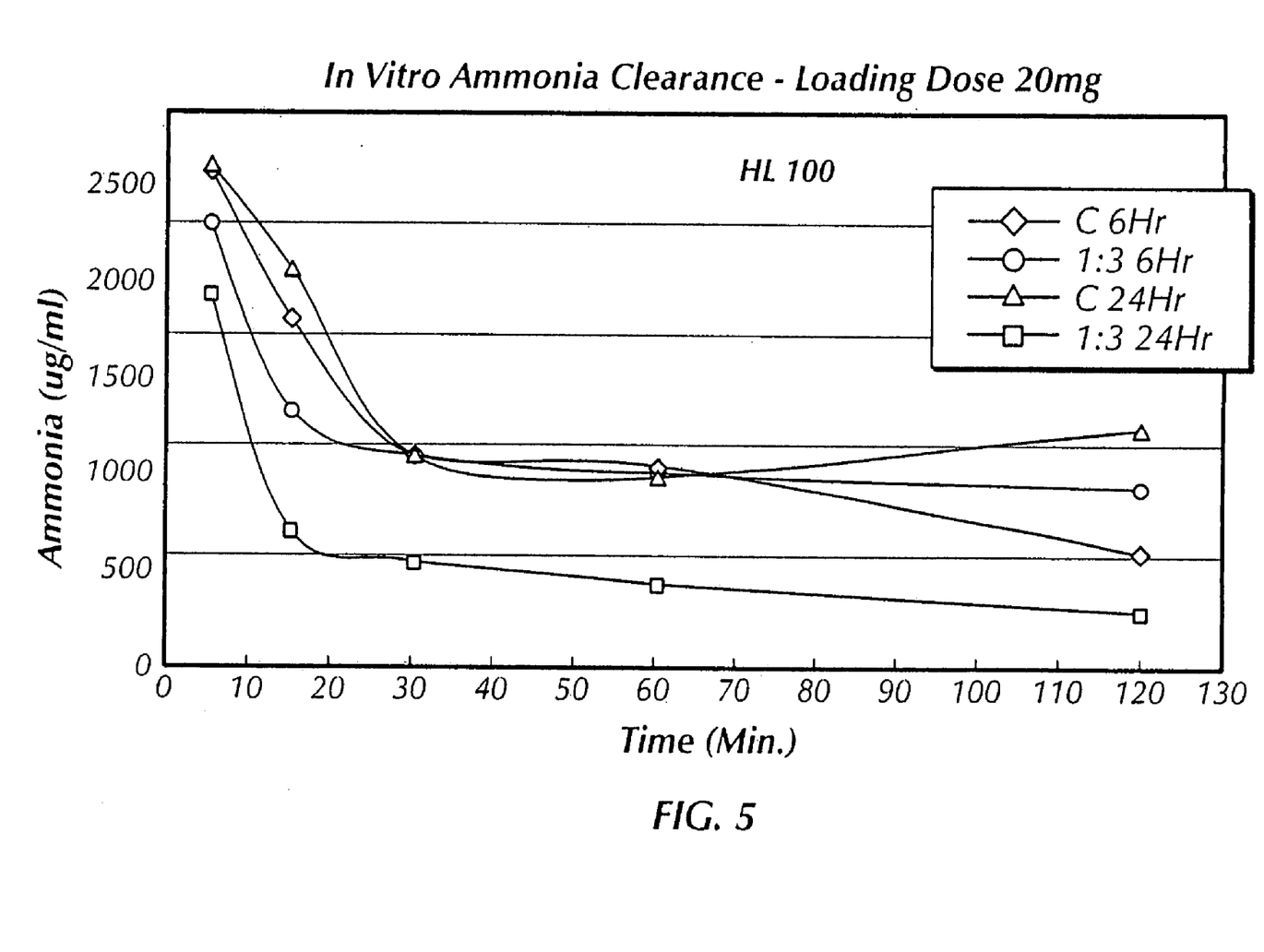
FIG. 5 is a graphical representation of in vitro ammonia clearance with a 6 hour and a 24 hour run using the bioartificial organ system of the present invention.

FIG. 5 is a graphical representation of in vitro ammonia clearance of a 20 mg loading dose. At approximately 30 minutes maximal ammonia clearance was observed in all trials. These results demonstrate the ability of the present invention to remove ammonia relatively quickly to non-toxic levels in the presence of drug candidate HL 100. In addition, there was no significant difference between the trials with continuous perfusion and those with intermittent perfusion, thereby indicating that less medium can be used while still retaining activity and efficiency of the device.

While the present invention has been illustrated and described by means of a specific embodiment, it is to be understood that numerous changes and modifications can be made therein without departing from the scope of the invention as defined in the accompanying claims.

The invention claimed is:

1. A system for testing potential drug candidates comprising, in combination:
an organ slice culture apparatus having:
a chamber comprising a medium inlet/outlet and a gas valve for supplying and discharging a gas;
a plurality of organ slices positioned within said chamber so as to maximize the surface area of said organ slices exposed to a medium; wherein said medium inlet/outlet is a means that both supplies said medium to said chamber so that said medium in said chamber completely immerses said organ slices and removes said medium from contact with said organ slices;
wherein said medium inlet/outlet is located at the bottom of said chamber below the position of said plurality of organ slices; and a reservoir connected to said inlet/outlet that contains said medium supplied and removed from said chamber; wherein when said organ slices are exposed to said potential drug candidate, the toxicity of said potential drug candidate can be determined by observing the effectiveness of said organ slices to metabolize a metabolizable compound in the presence of said potential drug candidate.

2. The system of claim 1, wherein a mesh partially surrounds said organ slices so as to form a space that retains said organ slices within said space, said mesh being approximately vertical in said chamber.

3. The system of claim 2, wherein each of said organ slices are retained between two meshes that respectively come into contact with opposing surfaces of said organ slices.

4. The system of claim 1, wherein the organ slices have a thickness in the range of about 10 μm to about 2,000 μm.

5. The system of claim 1, wherein the organ slices have a thickness in the range of about 100 μm to about 500 μm.

6. The system of claim 1, further comprising a means for introducing a gas to the gas valve.

7. The system of claim 6, wherein said gas is a mixture of oxygen and carbon dioxide.

8. The system of claim 1, further comprising an immunological filter inserted in said gas valve.

9. The system of claim 1, wherein said chamber is sealable.

10. The system of claim 9, wherein said chamber is thermoregulated.

11. The system of claim 1, wherein said compound is selected from the group consisting of ammonia and lidocaine.

* * * * *